United States Patent
Beck et al.

(10) Patent No.: US 8,472,021 B2
(45) Date of Patent: Jun. 25, 2013

(54) PARTICLE DETECTOR

(75) Inventors: Markus E. Beck, Scotts Valley, CA (US); Robert Green, Campbell, CA (US); Raffi Garabedian, Los Altos, CA (US); Erel Milshtein, Cupertino, CA (US); Ming Lun Yu, Fremont, CA (US)

(73) Assignee: First Solar, Inc., Perrysburg, OH (US)

( * ) Notice: Subject to any disclaimer, the term of this patent is extended or adjusted under 35 U.S.C. 154(b) by 161 days.

(21) Appl. No.: 13/082,796

(22) Filed: Apr. 8, 2011

(65) Prior Publication Data

US 2011/0249263 A1 Oct. 13, 2011

Related U.S. Application Data

(60) Provisional application No. 61/322,658, filed on Apr. 9, 2010.

(51) Int. Cl.
*G01N 21/00* (2006.01)
(52) U.S. Cl.
USPC .......................................... 356/342

(58) Field of Classification Search
USPC .......................................... 356/342
See application file for complete search history.

(56) References Cited

U.S. PATENT DOCUMENTS

| | | | |
|---|---|---|---|
| 4,739,177 A | 4/1988 | Borden | |
| 5,255,089 A | 10/1993 | Dybas et al. | |
| 6,346,425 B1 | 2/2002 | Ito et al. | |
| 7,006,682 B1 * | 2/2006 | Moriya et al. | 382/145 |
| 2002/0046941 A1 | 4/2002 | Takigawa et al. | |
| 2003/0054655 A1 | 3/2003 | Nakano et al. | |
| 2004/0063154 A1 * | 4/2004 | Booth et al. | 435/7.1 |

FOREIGN PATENT DOCUMENTS

| | | |
|---|---|---|
| EP | 0 321 265 A2 | 6/1989 |
| EP | 0 837 315 A2 | 4/1998 |
| EP | 1 855 081 A1 | 11/2007 |
| JP | 57-118630 A | 7/1982 |
| WO | WO 01/36937 A1 | 5/2001 |

* cited by examiner

*Primary Examiner* — Tu Nguyen
(74) *Attorney, Agent, or Firm* — Dickstein Shapiro LLP

(57) ABSTRACT

A particle detector for evaporation flux is disclosed. The particle detector includes a light source and at least one reflective surface.

32 Claims, 11 Drawing Sheets

PARTICLE DETECTOR

CROSS-REFERENCE TO RELATED APPLICATIONS

This application claims priority to U.S. Provisional Application Ser. No. 61/322,658, which was filed on Apr. 9, 2010, and is herein incorporated by reference in its entirety.

TECHNICAL FIELD

This invention relates to a particle detector for evaporation flux.

BACKGROUND

Light scattering can be used for particle detection in a gas or in vacuum environment. Known methods of particle detection can be inefficient, can introduce contamination, or can suffer from other shortcomings.

DETAILED DESCRIPTION

Figure 1:
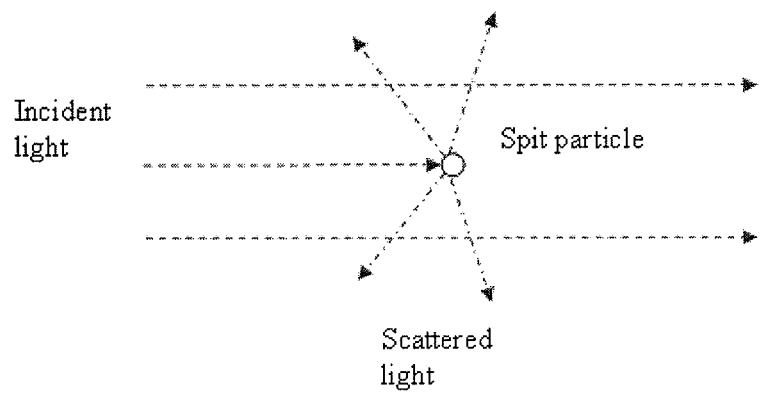
FIG. 1 is a diagram illustrating a light beam scattered by a spit particle.

Light scattering can be used for particle detection in a gas or vacuum environment. Smoke detection and particle detection based on light scattering have been used in semiconductor processing. During the deposition of thin films by evaporation, molten droplets can be ejected from the melt of the source material. This phenomenon is commonly called "spitting" and can be detrimental to the deposited films. For many industrial applications, either upward or downward evaporation deposition may be the preferred choice. Spit particulates can be monitored by optical inspection of the deposited film. A particle detector for evaporation flux and related method are developed to monitor the spit particulates in real time.

Advantageously, contamination by an evaporation flux can be avoided and collection of the scattering signal can be maximized. Indeed, no optical components other than reflective surfaces are needed inside the evaporation/deposition chamber.

In one aspect, a particle detector for evaporation flux in a deposition chamber can include a light source and a first reflective surface. The light source can generate a light beam to pass through an evaporation flux. The light source can be positioned outside of the deposition chamber. The light source can direct the light beam through a first window in a deposition chamber wall. The evaporation flux can scatter a portion of the light beam. The first reflective surface can be positioned in the deposition chamber to direct the scattered portion of the light beam through a second window on the chamber wall to a photo-detector. The photo-detector can measure the intensity of the scattered portion of the light beam.

The particle detector can include a beam stop to absorb the un-scattered portion of the light beam. The particle detector can include a second reflective surface to transfer the scattered portion of the light beam into a collimated light beam traveling toward the first reflective surface. The second reflective surface can include a parabolic mirror with a shape of a circular paraboloid. The particle detector can include a third reflective surface to direct the light beam from the light source to the evaporation flux. The particle detector can include a lens to focus the scattered portion of the light beam on the photo-detector. The particle detector can include a color filter positioned in front of the photo-detector to filter ambient light before being detected by the photo-detector. The scattered portion of the light beam can be forward-scattered. The scattered portion of the light beam can be backward-scattered.

The particle detector can include a fourth reflective surface to direct the un-scattered portion of the light beam back to the evaporation flux. The evaporation flux scatters the light beam from the light source to generate a first scattered portion of the light beam and the evaporation flux scatters the light beam directed from the fourth reflective surface to generate a second scattered portion of the light beam. The first scattered portion of the light beam can be forward-scattered and the second scattered portion of the light beam is backward-scattered. The first scattered portion of the light beam can be backward-scattered and the second scattered portion of the light beam can be forward-scattered.

The first scattered portion and the second scattered portion of the light beam can be guided through the second window on the chamber wall to the photo-detector by the first reflective surface. The first scattered portion and the second scattered portion of the light beam can be transferred into a collimated light beam traveling toward the first reflective surface by the second reflective surface.

The light source can include a high power LED light source. The light source can include a laser diode. The light source can generate a light beam having a wavelength from 300 nm to 800 nm. The photo-detector can include a photo-diode detector. The photo-detector can include a photomultiplier.

In another aspect, a method of detecting particle for evaporation flux in a deposition chamber can include directing a light beam from a light source outside a deposition chamber, through a first window in a deposition chamber wall and toward an evaporation flux inside the deposition chamber, wherein the evaporation flux can scatter a portion of the light beam. The method can include directing the scattered portion of the light beam through a second window on the chamber wall to a photo-detector by a first reflective surface positioned in the chamber. The photo-detector can measure the intensity of the scattered portion of the light beam.

The method can include absorbing an un-scattered portion of the light beam by a beam stop. The method can include transferring the scattered portion of the light beam into a collimated light beam traveling toward the first reflective surface by a second reflective surface. The second reflective surface can include a parabolic mirror with a shape of a circular paraboloid. The method can include directing the light beam from the light source to the evaporation flux by a third reflective surface.

The method can include focusing the scattered portion of the light beam on the photo-detector by a lens. The method can include filtering ambient light before being detected by the photo-detector by a color filter positioned in front of the photo-detector. The method can include directing the un-scattered portion of the light beam back to the evaporation flux by a fourth reflective surface. The evaporation flux scatters the light beam from the light source to generate a first scattered portion of the light beam and the evaporation flux scatters the light beam directed from the fourth reflective surface to generate a second scattered portion of the light beam.

As shown in FIG. 1, scattering is a general physical process where some forms of radiation, such as light, sound, or moving particles, are forced to deviate from a straight trajectory by one or more localized non-uniformities in the medium through which they pass. This also includes deviation of reflected radiation from the angle predicted by the law of reflection. Forward scattering dominates in light scattering for dielectric particles which are only refractive. Backscattering dominates for particles that are highly reflective. Special output lenses can be used to collect forward scattered light and to avoid the on-axis un-scattered light. A diode laser is an example of a light source that can be used. The wavelength can be in the visible, for example, in the range of about 540-780 nm. A high power LED light source can also be used. An LED source can also be coupled to an optical fiber easily, making the light source compact and flexible.

Figure 2:
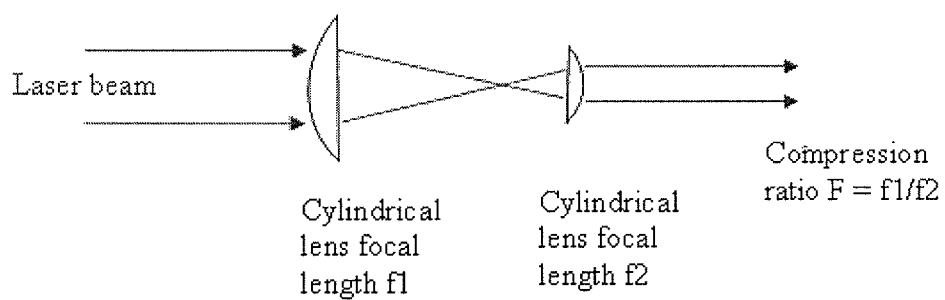
FIG. 2 is a diagram illustrating an optic configuration of a particle detector.
Figure 3:
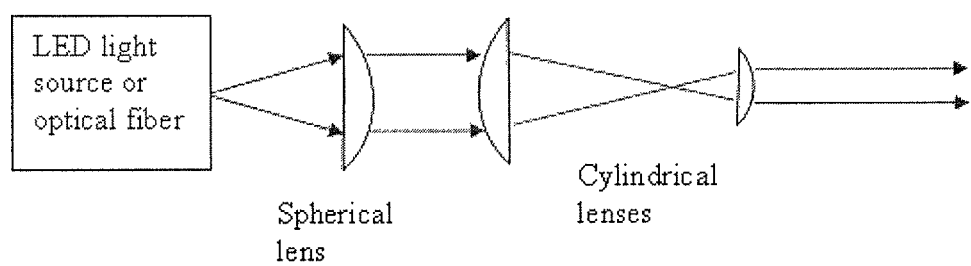
FIG. 3 is a diagram illustrating an optic configuration of a particle detector.

Since the signal intensity is linear with the light intensity, the signal can be boosted by simply compressing the beam. The compression can be in the direction of the particle motion. The beam is not compressed in the orthogonal direction because the width of the beam needs to be maintained to intercept the particle flux. Two prisms can be used to compress the beam. Beam compression in one-dimension can also be achieved with cylindrical lenses. There are two cases: parallel light beam from diode laser (shown in FIG. 2) and light beam from optical filter or LED (shown in FIG. 3). Referring to FIG. 2, the width of the beam in the orthogonal direction is preserved. Referring to FIG. 3, the diverging beam from the LED or optical fiber is first collimated by the spherical lens. After that, with the same arrangement as in the diode laser case, the beam is compressed in the particle motion direction. The width of the beam in the orthogonal direction is given by the width after the spherical lens.

To improve the signal to noise, the un-scattered light beam (dark-field) can be avoided. The incident beam can be prevented from hitting any edges. The un-scattered beam can be either directly absorbed by a beam stop or first reflected by a mirror into a beam stop. A "beam stop" can include any suitable barrier, screen, or filter capable of absorbing or blocking all or a portion of a light beam. Furthermore, a color filter can be used to filter or reduce ambient stray light.

The scattered light can be detected normal to the incident light path so that it is in the dark-field condition. Special output lenses can be used to collect forward scattered light and to avoid the on-axis un-scattered light. To further improve the collection of the scattered light, parabolic mirrors can be used with a shape of a circular paraboloid. Since the interaction volume is placed at the focus of the parabolic mirror, the forward scattered light can be reflected as a parallel beam, which can then be focused with another parabolic mirror or a converging lens onto the light detector.

Figure 4:
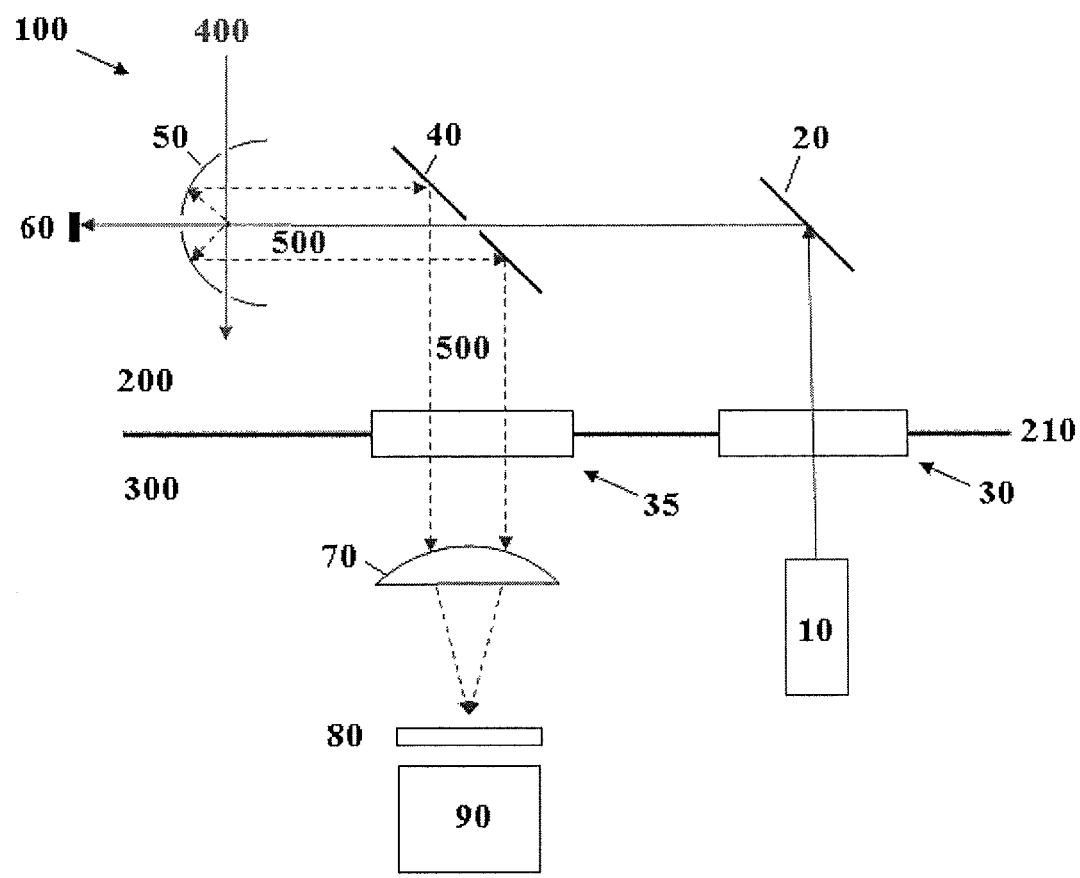
FIG. 4 is a diagram illustrating a configuration of a particle detector.

In some embodiments, referring to FIG. 4, particle detector 100 for evaporation flux in can include light source 10. Light source 10 can be positioned in outside space 300 of deposition chamber 200 and generate a light beam. The light beam can be directed through window 30 on chamber wall 210. Evaporation flux 400 can scatter a portion of the light beam. Mirror 40 can be positioned in chamber 200 to direct scattered portion 500 of the light beam through window 35 on chamber wall 210 to photo-detector 90. Specifically, a collimated light beam such as the light beam from light source 10 can be reflected by mirror 20, pass through a hole in mirror 40 and further through evaporation flux 400. A small hole is made at the apex of parabolic mirror 50 to let the un-scattered beam through to beam stop 60 without scattering at the edge of the hole. Two holes can be made on parabolic mirror 50 to let through evaporation flux 400 with the spit particulates to intercept the light beam. The sampling volume is the overlapping volume of these two fluxes. Scattered light 500 can be reflected by parabolic mirror 50 into a parallel beam. The inclined mirror 40 can reflect this beam through window 35 on evaporation chamber wall 210 onto focusing lens 70 outside. Scattered light beam 500 passes through color filter 80 to remove any ambient light before being detected by photo-detector 90. Photo-detector 90 can be a photodiode detector or a photomultiplier (PMT).

Photodiodes has the advantage that they are compact and do not require high voltages. The drawback is that their gain is less than that of the PMT. PMT has higher gain but it requires a high voltage to operate. In either case, the detector should be selected for sensitivity at the incident light wavelength. The gain can be high but remain in the linear range. The spit particulate flux density is derived from the particle count. The particle size is related to the pulse height.

The pulse height is a representation of the particle size. However the scale is not linear. It is also particle shape dependent as the particulates may not be spherical. The particle sizes can be calibrated with spherical polystyrene latex (PSL) spheres. The particle sizes can be "PSL equivalent" sizes.

Figure 5:
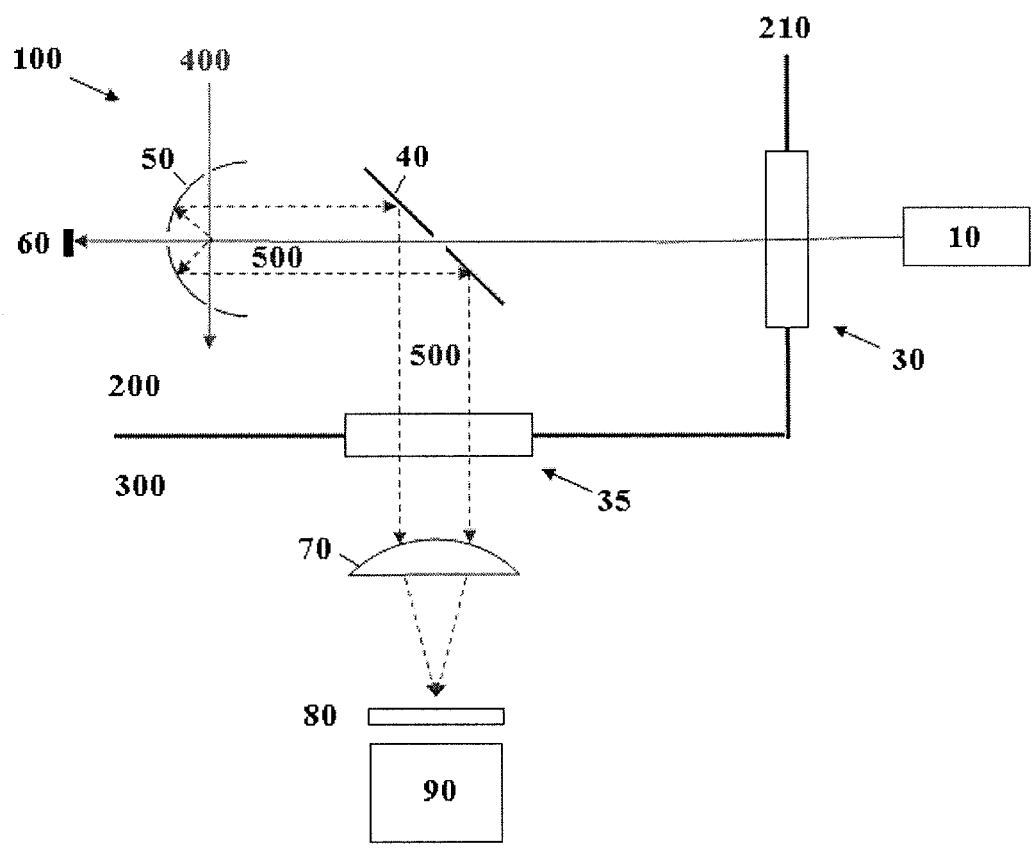
FIG. 5 is a diagram illustrating a configuration of a particle detector.

In some embodiments, referring to FIG. 5, light source 10 can be positioned to direct the light beam pass through a hole in mirror 40 and further through evaporation flux 500 without mirror 20 in FIG. 4.

Figure 6:
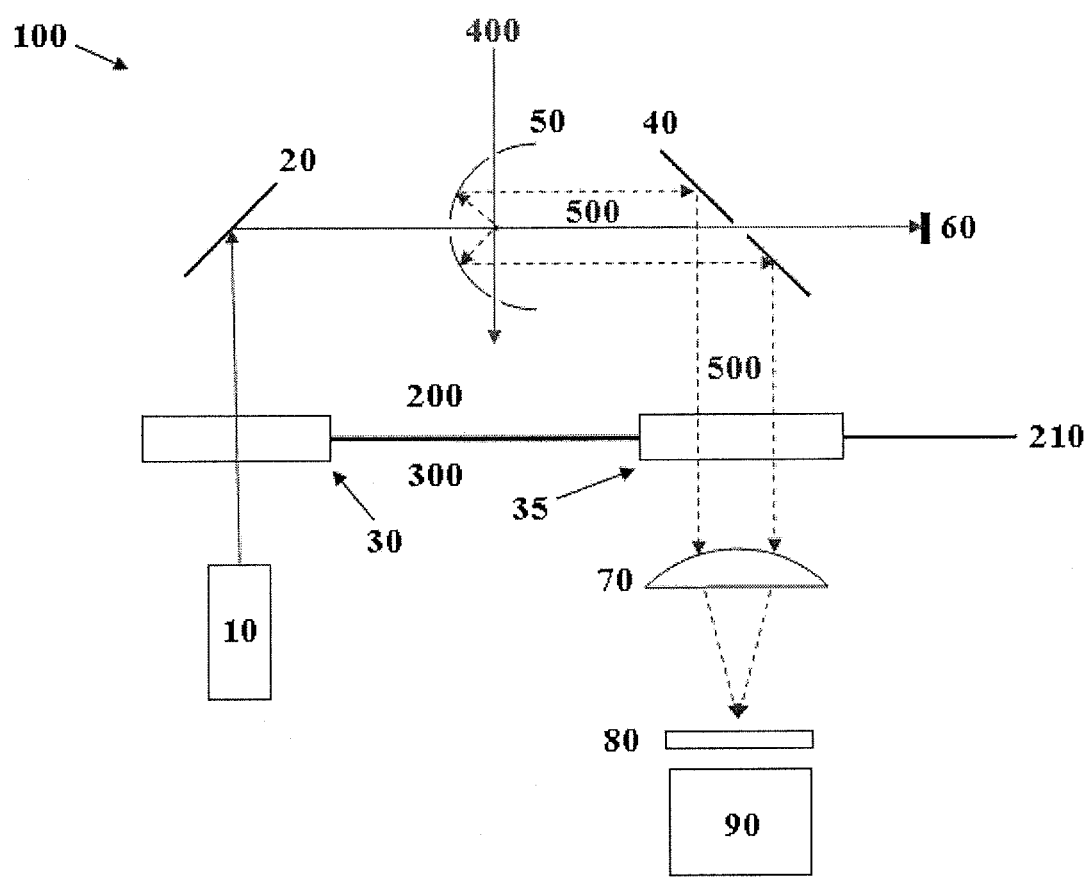
FIG. 6 is a diagram illustrating a configuration of a particle detector.

For particles, such as metallic particles, most of scattering are backward scattering. Referring to FIG. 6, the beam path can be reversed to collect the backscattered light.

Figure 7:
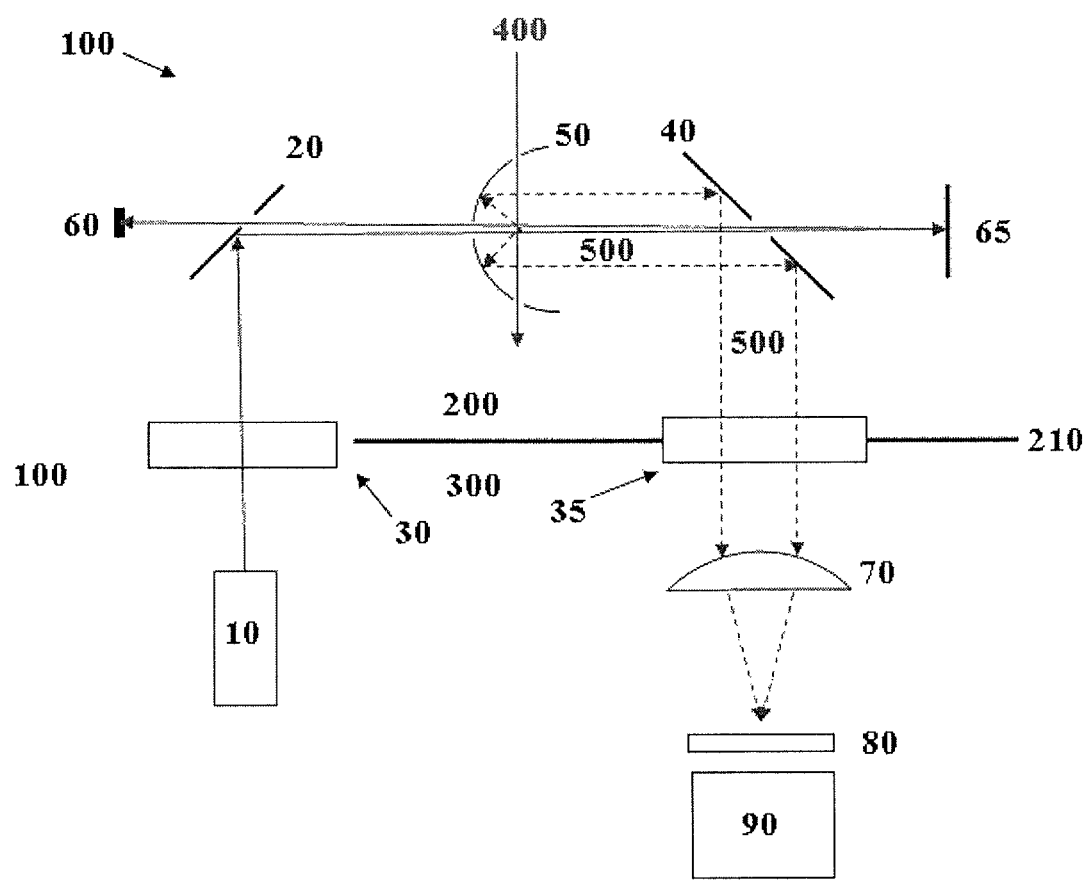
FIG. 7 is a diagram illustrating a configuration of a particle detector.

In some embodiments, referring to FIG. 7, beam stop 60 can be replaced by mirror 65 to return the un-scattered beam at a slightly off-angle, both forward scattering and backscattering portion 500 of the light beam can be directed to photo-detector 90.

Furthermore, it has been recognized that a larger width of the beam orthogonal to the particle motion helps to intersect more particles. However, an increase in the lateral width also decreases the light intensity. To overcome with this dilemma, opposing mirrors (140 and 130 in FIG. 8) can be used to generate a nest of beam paths (laser beam curtain) using multiple reflection. With the parabolic mirror arrangement, the beam curtain can be used to enhance the collection of both the forward scattered and backscattered light intensities, thus extending the utility of the particle detector to more kinds of particulates.

Figure 8:
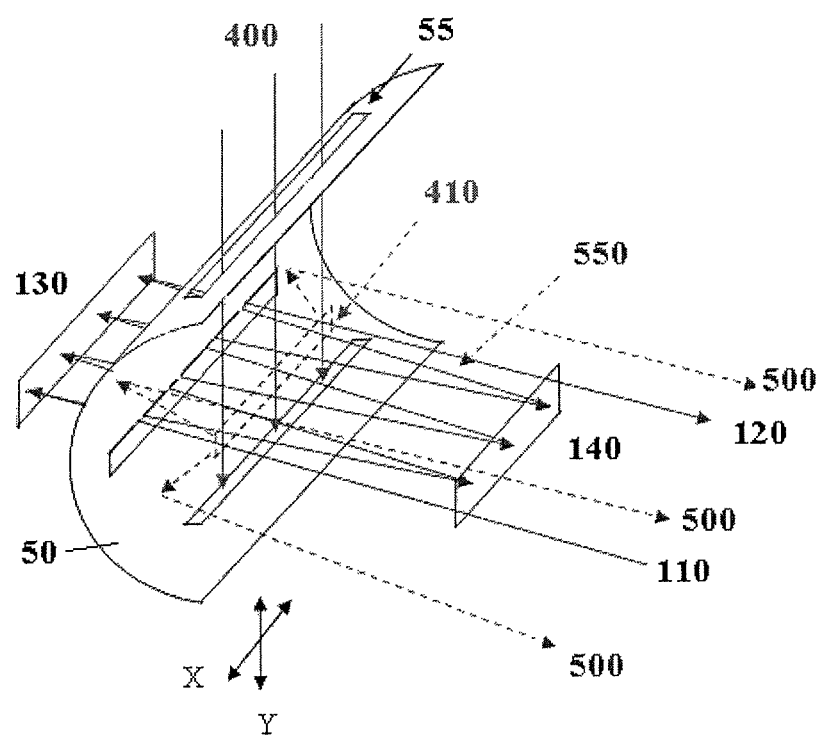
FIG. 8 is a diagram illustrating a configuration of a particle detector.

Referring to FIG. 8, collimated incident light 110 can be directed to evaporation flux 400. When curtain beam 550 is foamed between two plane mirrors 130 and 140, one-dimensional parabolic mirror 50 with the curtain along the linear focus (X-direction) can be suitable. Slits 55 are cut on parabolic mirror 50 to let through the evaporation flux 400 with the spit particulates. The intersection of the current beam and the evaporation flux 400 can define linear sampling volume 410 in the X-direction. Finally, unscattered beam 120 can be directed to a beam stop (not shown in FIG. 8).

Figure 9:
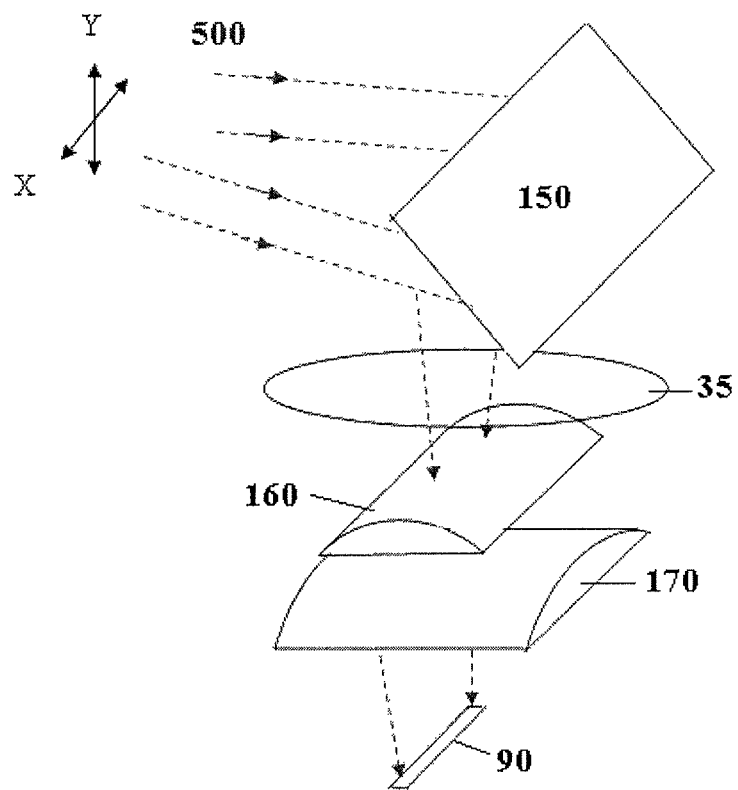
FIG. 9 is a diagram illustrating a configuration of a particle detector.

The scattered light can be reflected into a parallel beam with a spread in the Y-direction, but there will be divergence in the X-direction. Referring to FIG. 9, plane mirror 150 can be used as before to reflect scattered light 500 through window 35 on the chamber wall to the outside of the chamber. Two cylindrical mirrors 160 and 170 can used to refocus the rays in both the X and Y directions. In some embodiments, the present invention can focus the scattered light into a focus into a photo-detector to have an integrated monitor of all the spit particulates in the sample volume. In other embodiments, the present invention can form an image of the sampling volume onto a 1-dimensional photo-detector to monitor the spatial distribution of the spit particulates if necessary.

With the particle detector of real-time monitoring, spitting can be minimized by proper outgassing of the source material. Heating uniformity can be another factor. Therefore, the evaporation sources can be tuned to minimize spitting before film production. In some embodiments, the particle detector can be mounted on a retractable set up. It is inserted into the vapor plume for the detection of particulates. It is then retracted after the evaporation conditions are set.

Figure 10:
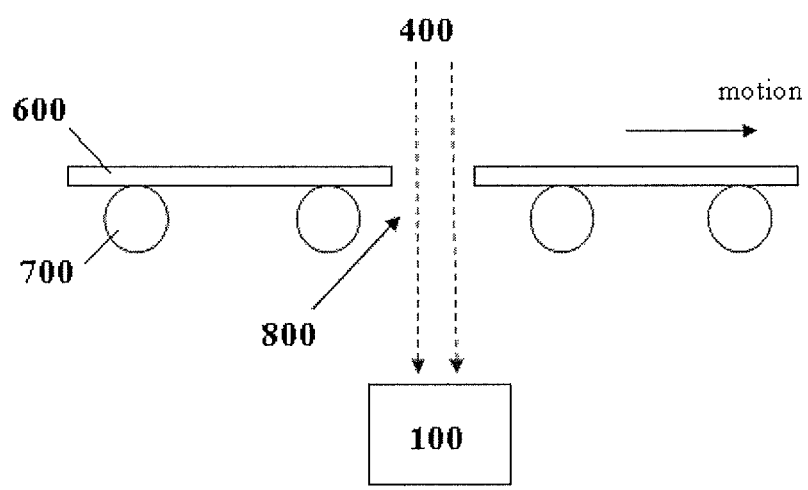
FIG. 10 is a diagram illustrating a configuration of a particle detector.

In some embodiments, referring to FIG. 10, during downward film deposition, substrates 600 can be usually transported on conveyer 700 underneath the evaporation source. The moving substrates 600 can shutter the flux on and off There can be gap 800 in between the substrates. Gap 800 can be used for the monitoring of particulates flux 400. Particle detector 100 can be placed underneath substrate 600. When gap 800 between substrates 600 is directly above particle detector 100, particle detector 100 can give the particle counts plus the background counts $N_{gap}$. The integration time is (gap length)/(motion speed).

When substrate 600 is above particle detector 100, evaporation flux 400 is blocked. So the counts $N_{sub}$ registered by particle detector 100 will all be background counts. These background counts are the sum of electronic noise and particulates from the conveyer and other sources. The integration time=(substrate length)/(motion speed). Therefore, the particle count rate in the evaporation flux can be calculated by the following equation: particle count rate=motion speed*[$N_{gap}$/(gap length)–$N_{sub}$/(substrate length)]. As a result, the particle detector can accurately monitor evaporation flux in any suitable environment, including an environment such as a deposition chamber that has a moving series of substrates on which material is being deposited.

Figure 11:
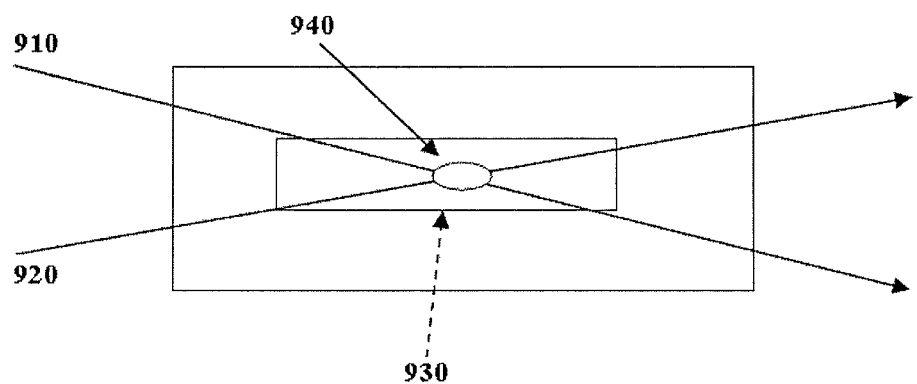
FIG. 11 is a diagram illustrating a configuration of a particle detector.

Further information about the spits can also be obtained by changing other experimental parameters. For example, multi-wavelength scattering measurement can be used to evaluate spit size and location. In one embodiment, this measurement can be taken with three different discrete lasers of sufficient power. As shown in FIG. 11, multi-angle light can be directed from two or more light sources and aimed at covering similar areas on the evaporation flux plume path. This can help for generating a degree of redundancy of the measurement as well as obtaining the 3D shape information of the spits. Referring to FIG. 11, a multi-angle light beam can be generated from two light sources (910 and 920) and aimed a location 930 of evaporation flux 940 path. Polarized light can be used at two angles to measure more particle/spit attributes such as surface smoothness. Using pulsed light can increase the detectability of the spit by separating the signal coming or reducing from the spit from the background signal.

A number of embodiments of the invention have been described. Nevertheless, it will be understood that various modifications may be made without departing from the spirit and scope of the invention. It should also be understood that the appended drawings are not necessarily to scale, presenting a somewhat simplified representation of various preferred features illustrative of the basic principles of the invention.

What is claimed is:

1. A particle detector for evaporation flux in a deposition chamber, comprising:
   a light source generating a light beam to pass through an evaporation flux, wherein the light source is positioned outside of a deposition chamber, directing the light beam through a first window in a deposition chamber wall, the evaporation flux scattering a portion of the light beam;
   a first reflective surface positioned in the deposition chamber to direct the scattered portion of the light beam through a second window on the chamber wall to a photo-detector, wherein the photo-detector measures the intensity of the scattered portion of the light beam; and
   a second reflective surface to transfer the scattered portion of the light beam into a collimated light beam traveling toward the first reflective surface.

2. The particle detector of claim 1, further comprising a beam stop to absorb the un-scattered portion of the light beam.

3. The particle detector of claim 2, wherein the second reflective surface comprises a parabolic mirror with a shape of a circular paraboloid, and the parabolic mirror further comprises a hole at the apex of the parabolic mirror that is aligned with the beam stop.

4. The particle detector of claim 3, wherein the parabolic mirror further comprises two holes that allow the evaporation flux to intercept the light beam.

5. The particle detector of claim 1, further comprising a third reflective surface to direct the light beam from the light source to the evaporation flux.

6. The particle detector of claim 1, further comprising a lens to focus the scattered portion of the light beam on the photo-detector.

7. The particle detector of claim 1, further comprising a color filter positioned in front of the photo-detector to filter ambient light before being detected by the photo-detector.

8. The particle detector of claim 1, wherein the scattered portion of the light beam is forward-scattered.

9. The particle detector of claim 1, wherein the scattered portion of the light beam is backward-scattered.

10. The particle detector of claim 1, wherein the light source is selected from the group consisting of a high power LED light source, and a laser diode.

11. The particle detector of claim 1, wherein the light source generates a light beam having a wavelength from 300 nm to 800 nm.

12. The particle detector of claim 1, wherein the photo-detector is selected from the group consisting of a photodiode detector and a photomultiplier.

13. The particle detector of claim 1, wherein the first reflective surface further comprises a hole that is aligned with the light beam.

14. The particle detector of claim 1, wherein the second reflective surface further comprises a horizontal slit that is aligned with the light beam; and the particle detector further comprises a fourth reflective surface located behind the second reflective surface and aligned with the horizontal slit, and a fifth reflective surface located in front of the second reflective surface and aligned with the horizontal slit.

15. The particle detector of claim 14, wherein the light beam forms a curtain beam between the fourth and fifth reflective surfaces.

16. The particle detector of claim 14, wherein the second reflective surface further comprises two slits that allow the evaporation flux to intercept the light beam.

17. A particle detector for evaporation flux in a deposition chamber, comprising:
   a light source generating a light beam to pass through an evaporation flux, wherein the light source is positioned outside of a deposition chamber, directing the light beam through a first window in a deposition chamber wall, the evaporation flux scattering a portion of the light beam;
   a first reflective surface positioned in the deposition chamber to direct the, scattered portion of the light beam through a second window on the chamber wall to a photo-detector, wherein the photo-detector measures the intensity of the scattered portion of the light beam; and
   a second reflective surface to direct the un-scattered portion of the light beam back to the evaporation flux, wherein the evaporation flux scatters the light beam from the light source to generate a first scattered portion of the light beam and the evaporation flux scatters the light beam directed from the second reflective surface to generate a second scattered portion of the light beam.

18. The particle detector of claim 17, wherein the first scattered portion of the light beam is forward-scattered and the second scattered portion of the light beam is backward-scattered.

19. The particle detector of claim 17, wherein the first scattered portion of the light beam is backward-scattered and the second scattered portion of the light beam is forward-scattered.

20. The particle detector of claim 17, wherein the first scattered portion and the second scattered portion of the light beam are guided through the second window on the chamber wall to the photo-detector by the first reflective surface.

21. The particle detector of claim 20, wherein the first scattered portion and the second scattered portion of the light beam are transferred into a collimated light beam traveling toward the first reflective surface by a third reflective surface.

22. A method of detecting particles for evaporation flux in a deposition chamber, comprising:
   directing a light beam from a light source outside a deposition chamber through a first window in a deposition chamber wall and toward an evaporation flux inside the deposition chamber, wherein the evaporation flux scatters a portion of the light beam;
   forming, by a second reflective surface, the scattered portion of the light beam into a collimated light beam traveling toward a first reflective surface; and
   directing the scattered portion of the light beam through a second window on the chamber wall to a photo-detector by the first reflective surface, wherein the photo-detector measures the intensity of the scattered portion of the light beam.

23. The method of claim 22, further comprising absorbing an un-scattered portion of the light beam by a beam stop.

24. The method of claim 23, wherein the second reflective surface comprises a parabolic mirror with a shape of a circular paraboloid, and the parabolic mirror comprises a hole at the apex of the parabolic mirror that is aligned with the beam stop.

25. The method of claim 22, further comprising directing the light beam from the light source to the evaporation flux by a third reflective surface.

26. The method of claim 22, further comprising focusing the scattered portion of the light beam on the photo-detector by a lens.

27. The method of claim 22, further comprising filtering ambient light before being detected by the photo-detector by a color filter positioned in front of the photo-detector.

28. A method of detecting particles for evaporation flux in a deposition chamber, comprising:
   directing a light beam from a light source outside a deposition chamber through a first window in a deposition chamber wall and toward an evaporation flux inside the deposition chamber, wherein the evaporation flux scatters a portion of the light beam;
   directing the scattered portion of the light beam through a second window on the chamber wall to a photo-detector by a first reflective surface positioned in the chamber, wherein the photo-detector measures the intensity of the scattered portion of the light beam; and
   directing the un-scattered portion of the light beam back to the evaporation flux by a second reflective surface, wherein the evaporation flux scatters the light beam from the light source to generate a first scattered portion of the light beam and the evaporation flux scatters the light beam directed from the second reflective surface to generate a second scattered portion of the light beam.

29. The method of claim 28, wherein the first scattered portion of the light beam is forward-scattered and the second scattered portion of the light beam is backward-scattered.

30. The method of claim 28, wherein the first scattered portion of the light beam is backward-scattered and the second scattered portion of the light beam is forward-scattered.

31. The method of claim 28, further comprising guiding, by the first reflective surface, the first scattered portion and the second scattered portion of the light beam through the second window on the chamber wall to the photo-detector.

32. The method of claim 31, further comprising forming, by a third reflective surface, the first scattered portion and the second scattered portion of the light beam into a collimated light beam traveling toward the first reflective surface.

* * * * *